United States Patent
Saalbach et al.

(10) Patent No.: US 10,503,774 B2
(45) Date of Patent: Dec. 10, 2019

(54) MEDICAL SELECTION SYSTEM

(71) Applicant: KONINKLIJKE PHILIPS N.V., Eindhoven (NL)

(72) Inventors: Axel Saalbach, Hamburg (DE); Julien Senegas, Hamburg (DE); Michael Chun-chieh Lee, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 687 days.

(21) Appl. No.: 14/374,990

(22) PCT Filed: Jan. 14, 2013

(86) PCT No.: PCT/IB2013/050325
§ 371 (c)(1),
(2) Date: Jul. 28, 2014

(87) PCT Pub. No.: WO2013/111033
PCT Pub. Date: Aug. 1, 2013

(65) Prior Publication Data
US 2015/0006574 A1    Jan. 1, 2015

Related U.S. Application Data

(60) Provisional application No. 61/591,328, filed on Jan. 27, 2012.

(51) Int. Cl.
*G06F 16/00*      (2019.01)
*G06F 16/532*     (2019.01)
(Continued)

(52) U.S. Cl.
CPC .......... *G06F 16/532* (2019.01); *G06F 19/321* (2013.01); *G06T 7/0016* (2013.01); *G06T 2207/30004* (2013.01)

(58) Field of Classification Search
None
See application file for complete search history.

(56) References Cited

U.S. PATENT DOCUMENTS

| 7,912,733 B2 * | 3/2011 | Clements | G06F 19/322 705/2 |
| 8,208,703 B2 | 6/2012 | Kawagishi et al. | |

(Continued)

FOREIGN PATENT DOCUMENTS

| JP | H04333971 A | 11/1992 |
| JP | 2000342576 A | 12/2000 |

(Continued)

OTHER PUBLICATIONS

AutoRescan Quick Guide. www.heidelbergengineering.com/wp-content/uploads/2095_Product-Lit_AutoRescan-Quick-Guide_LOWRES.PDF.

(Continued)

*Primary Examiner* — Bai D Vu

(57) ABSTRACT

A medical selection system 100 for generating selection data includes a user input 110 for enabling a user to establish a selection of one or more medical images amongst a plurality of medical images 182 for establishing the one or more medical images as baseline images for use in a follow-up examination of a patient. A processor 120 generate selection data 132 being indicative of said selection, and includes selection metadata in the selection data for enabling associating the selection data with the plurality of medical images. An output 130 provides the selection data to a medical processing system 150 for enabling the medical processing system to select, based on the selection data, the one or more medical images amongst the plurality of medical images for use as the baseline images in the follow-up examination of the patient.

20 Claims, 1 Drawing Sheet

(51) Int. Cl.
*G06F 19/00* (2018.01)
*G06T 7/00* (2017.01)

(56) References Cited

U.S. PATENT DOCUMENTS

| | | | |
|---|---|---|---|
| 8,840,557 B2 | 9/2014 | Casclaro et al. | |
| 8,867,807 B1* | 10/2014 | Fram | G06F 19/321 382/128 |
| 9,129,049 B2 | 9/2015 | Miyazawa et al. | |
| 2003/0018245 A1 | 1/2003 | Kaufman et al. | |
| 2006/0242149 A1* | 10/2006 | Richard | G06F 19/324 |
| 2007/0067185 A1 | 3/2007 | Halsted | |
| 2007/0118540 A1 | 5/2007 | Dongbai | |
| 2007/0239489 A1* | 10/2007 | Masuzawa | G06F 19/321 705/3 |
| 2009/0054755 A1* | 2/2009 | Shiibashi | G06F 19/321 600/407 |
| 2009/0103789 A1 | 4/2009 | Danner et al. | |
| 2010/0049740 A1* | 2/2010 | Iwase | G06F 19/321 705/7.27 |
| 2010/0317967 A1 | 12/2010 | Carlsen et al. | |
| 2011/0225000 A1* | 9/2011 | Selim | G06F 19/328 705/2 |
| 2012/0323593 A1* | 12/2012 | Backhaus | G06F 19/321 705/2 |
| 2013/0060579 A1* | 3/2013 | Yu | G06Q 10/06 705/3 |

FOREIGN PATENT DOCUMENTS

| | | |
|---|---|---|
| JP | 2001202501 A | 7/2001 |
| JP | 2004275499 A | 10/2004 |
| JP | 2005293059 A | 10/2005 |
| JP | 2009064255 A | 3/2009 |
| JP | 2011081512 A | 4/2011 |
| WO | 2008154741 A1 | 12/2008 |

OTHER PUBLICATIONS

Fischer, B. et al. "Integration of a research CBIR system with RIS and PACS for radiological routine". Proceedings of SPIE, SPIE—International Society for Optical Engineering, Bellingham, WA., vol. 6919, (2008), pp. 1-10.

* cited by examiner

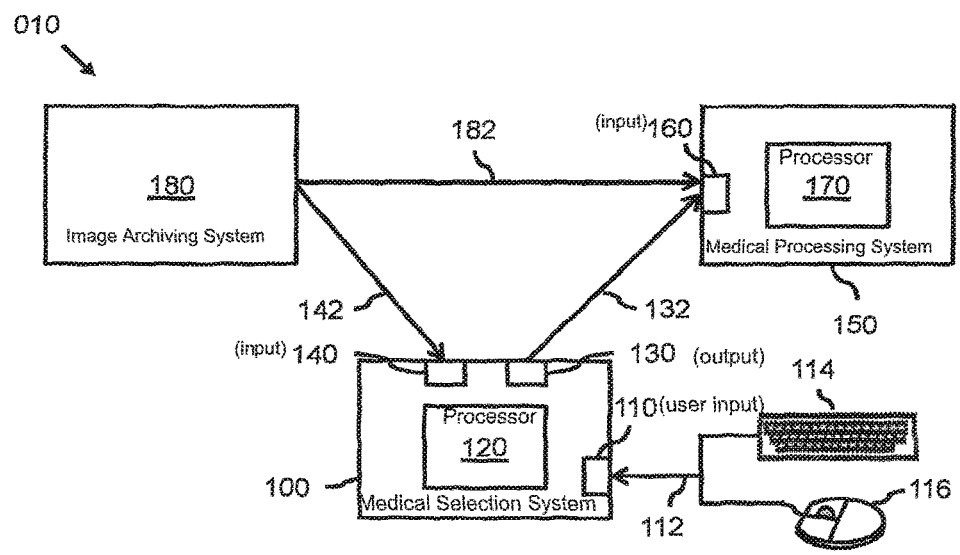
Fig. 1
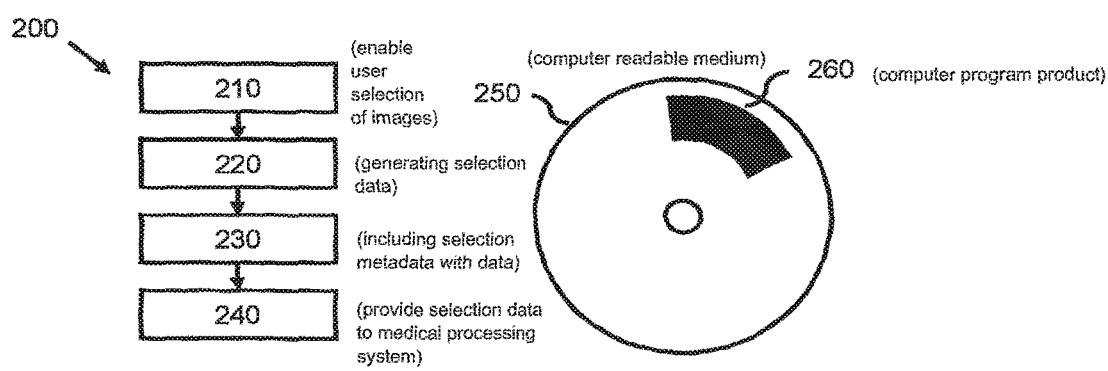
Fig. 2
Fig. 3

MEDICAL SELECTION SYSTEM

This application is a national stage application under 35 U.S.C. § 371 of International Application No. PCT/IB2013/050325 filed on Jan. 14, 2013 and published in the English language on Aug. 1, 2013 as International Publication No. WO/2013/111033, which claims priority to U.S. Application No. 61/591,328 filed on Jan. 27, 2012, the entire disclosures of which are incorporated herein by reference.

FIELD OF THE INVENTION

The invention relates to a medical selection system and a method of generating selection data. The invention further relates to a medical processing system, and a workstation and imaging system comprising the medical selection system or the medical processing system. The invention further relates to a computer program product comprising instructions for causing a processor system to perform the method set forth. A medical examination of a patient may involve obtaining a first set of medical images of a patient at a first instance in time, obtaining a second set of medical images at a later instance in time, and comparing both sets of medical images to determine, e.g., whether the patient responds to a treatment, whether a tissue grows over time, etc.

The medical images of the first set are typically referred to as baseline images, and serve for establishing a baseline of the patient, i.e., a state of the patient at said first instance in time. The medical images of the second set are typically referred to as follow-up images and serve for establishing a follow-up of the patient, e.g., the state of the patient at said later instance in time. The follow-up images are typically obtained by performing a follow-up scan during a follow-up examination of the patient. Performing the follow-up scan may involve planning said scan using the baseline images so as to obtain follow-up images showing the same body part of the patient, having a similar scan geometry, etc.

Having obtained the follow-up images, a clinician typically determines a change in the state of the patient by visually comparing one or more of the baseline images with the follow-up images. Alternatively, or additionally, the differences between said one or more images may be determined automatically, e.g., using image analysis techniques.

BACKGROUND OF THE INVENTION

It is known to select one or more medical images amongst a plurality of medical images of a patient for establishing the one or more medical images as reference images, the reference images being used in a follow-up examination of the patient.

For example, a document "*AutoRescan Quick Guide*", as obtained from http://www.heidelbergengineering.com/wp-content/uploads/2095_Product-Lit_AutoRescan-Quick-Guide_LOWRES.PDF on Jan. 10, 2012, discloses that, after a baseline scan, a scan may be marked by clicking on an image and selecting 'Set Reference'. In a follow-up scan, the desired reference scan can then be chosen by a user from a drop down menu. It is noted that only scans that have been marked as reference appear in the menu list.

A problem of the aforementioned system is that the user needs to select the images as references on the same system that is used for taking the follow-up scan.

SUMMARY OF THE INVENTION

It would be advantageous to obtain a medical selection system or method for enabling a user to select one or more medical images separately from the medical processing system that is used in performing the follow-up examination of the patient.

To better address this concern, in a first aspect of the invention, a medical selection system is provided for generating selection data, the medical selection system comprising:

a user input for enabling a user to establish a selection of one or more medical images amongst a plurality of medical images for establishing the one or more medical images as baseline images for use in a follow-up examination of a patient;

a processor for (i) generating selection data being indicative of said selection, and (ii) including selection metadata in the selection data for enabling associating the selection data with the plurality of medical images; and an output for providing the selection data to a medical processing system for enabling the medical processing system to select, based on the selection data, the one or more medical images amongst the plurality of medical images for use as the baseline images in the follow-up examination of the patient.

In a further aspect of the invention, a medical processing system is provided for selecting one or more medical images amongst a plurality of medical images for use as baseline images in a follow-up examination of a patient, the medical processing system comprising:

an input for obtaining selection data from a medical selection system, the selection data being indicative of a selection by a user of the one or more medical images amongst the plurality of medical images; and a processor for (i) associating the selection data with the plurality of medical images, based on selection metadata included in the selection data, and (ii) selecting said one or more medical images, based on the selection data.

In a further aspect of the invention, a workstation and an imaging apparatus are provided comprising the medical selection system or the medical processing system set forth.

In a further aspect of the invention, a method is provided for generating selection data, comprising:

enabling a user to establish a selection of one or more medical images amongst a plurality of medical images for establishing the one or more medical images as baseline images for use in a follow-up examination of a patient;

generating selection data being indicative of said selection;

including selection metadata in the selection data for enabling associating the selection data with the plurality of medical images; and providing the selection data to a medical processing system for enabling the medical processing system to select, based on the selection data, the one or more medical images amongst the plurality of medical images for use as baseline images in a follow-up examination of the patient.

In a further aspect of the invention, a computer program product is provided comprising instructions for causing a processor system to perform the method set forth.

The medical selection system comprises a user input which allows a user to select one or more medical images from a plurality of medical images. The plurality of medical images may be from a single patient. The user selects the one or more medical images to establish a baseline for a follow-up examination that is to be performed of the patient. The selection thus involves the user determining which of the plurality of medical images are to be used as baseline images in the follow-up examination of the patient.

The medical selection system further comprises a processor which generates selection data, based on the selection. The selection data is a data representation of the selection from which it can be determined which of the plurality of medical images are selected. The processor generates the selection data as comprising additional metadata, such as a header, that allows the selection data to be matched to the plurality of medical images. Thus, having obtained the selection data and, e.g., multiple pluralities of images, the selection data can be associated with a particular one of the multiple pluralities of images.

The medical selection system further comprises an output that transmits the selection data to a medical processing system. The medical processing system is arranged for automatically selecting the one or more medical images amongst the plurality of medical images, based on the selection data. For receiving the selection data from the medical selection system, the medical processing system comprises an input. For determining for which plurality of medical images the selection data was generated, the medical processing system comprises a processor that associates the selection data with a particular plurality of medical images, based on the metadata included in the selection data.

By generating selection data based on a selection of the user, the selection of the user is encoded as data separately from the plurality of medical images. Thus, the selection can be transmitted or stored independently of the plurality of medical images. By including metadata that allows the selection data to be associated with said plurality of medical images, the selection can nevertheless be associated with the plurality of medical images despite being transmitted or stored independently. By providing a medical selection system that generates the selection data and a medical processing system that applies the selection data, a user can select the one or more medical images in separation of the medical processing system used in performing the follow-up examination of the patient.

The present invention is partially based on the recognition that selecting the one or more medical images on a medical processing system that is used in performing the follow-up examination of the patient is inconvenient, as the selection is preferably performed by a clinician, while the medical processing system typically is operated by a technician preparing and/or performing an examination such as the follow-up examination of said patient. An example of a medical processing system is a MR (Magnetic Resonance) or CT (Computed Tomography) scanner. Another example of a medical processing system is a workstation that is used for planning follow-up scans. Another example of a medical processing system is a RIS, short for Radiology Information System, being connected or connectable to said scanner. Hence, a technician may need to select the one or more medical images, based on input from the clinician. However, the selection then becomes error prone, as, e.g., the technician may misunderstand the clinician's input. Alternatively, the clinician may personally perform the selection on the medical processing system. However, the clinician then has to physically access the medical processing system, e.g., by entering an examination room. Disadvantageously, the clinician temporarily occupies the medical processing system, resulting in additional time needed between examinations as the technician is unable to prepare and/or perform examinations during such time.

The measures of the present invention enable a user such as the clinician to select the one or more medical images on a medical selection system that is separate from the medical processing system. The medical selection system may be located more conveniently for the user, e.g., in the clinician's office. The selection data is then transmitted to the medical processing system where the selection is automatically performed. Moreover, by providing selection metadata as part of the selection data, it is prevented that the selection data is erroneously applied to a wrong plurality of images. Advantageously, errors are avoided due to the technician having to select the one or more medical images. Advantageously, time between examinations is reduced as the clinician does not need to occupy the medical processing system in order to select the one or more medical images. Advantageously, a more convenient clinical workflow is provided for the clinician and the technician.

Optionally, the processor is arranged for generating the selection data having a format compatible with a pre-existing image communication standard. By providing the selection data in a format that is compatible with a pre-existing image communication standard, the selection data can be transmitted and stored without the need of modifying the medical selection system, the medical processing system, as well as the communication network between both systems. Advantageously, an existing communication infrastructure, e.g., within a hospital, may be re-used for transmitting and/or storing the selection data.

Optionally, the pre-existing image communication standard is DICOM. DICOM, short for Digital Imaging and COmmunications in Medicine, is a well-established standard for handling, storing, printing, and transmitting information in medical imaging. By generating the selection data having a format compatible with DICOM, an existing DICOM communication network may be used for transmitting and/or storing the selection data. Advantageously, the selection data may be received and stored by existing medical processing systems that are compatible with the DICOM communication standard.

Optionally, the processor is arranged for encoding the selection data in an instance of a DICOM Service-Object Pair Class. The selection data is thus encoded in a manner that conforms to the DICOM standard. Advantageously, by encoding the selection data in an instance of a DICOM Service-Object Pair Class, the selection data may be easily paired with the plurality of medical images by the medical processing system.

Optionally, the processor is arranged for encoding the selection data in an Information Object of said DICOM Service-Object Pair Class. Said manner of encoding is well suited for encoding the selection data in a DICOM Service-Object Pair Class.

Optionally, the medical selection system forms a DICOM application entity in a DICOM network comprising the medical processing system, and the output is a DICOM network interface of the DICOM application entity. The medical selection system is thus directly compatible with the DICOM network and does not need an additional interface.

Optionally, the medical selection system further comprises an input for obtaining image metadata of the plurality of medical images, the image metadata being indicative of contents of the plurality of medical images, wherein the processor is arranged for generating the selection metadata based on the image metadata. By generating the selection metadata based on the image metadata, the selection metadata is generated as also being indicative of the contents of the plurality of images. Advantageously, the selection data may be conveniently associated with the plurality of medical images by identifying whether the selection metadata and the image metadata are indicative of the same or similar content.

Optionally, the processor is arranged for generating the selection metadata by including at least a part of the image metadata. Including at least a part of the image metadata is a particularly suitable manner of generating the selection metadata, based on the image metadata. Advantageously, the selection data may be associated with the plurality of medical images by directly comparing parts or all of their respective metadata.

Optionally, the selection data comprises one of: a DICOM Unique Identifier (UID), a patient name, a study identifier, a series number, an intended use.

Optionally, in the medical processing system set forth, the input is arranged for obtaining the one or more medical images from an archiving system, based on the selection data. The medical processing system may obtain said images from an image archiving system such as a PACS, short for Picture Archiving and Communication System. Advantageously, the medical processing system may only obtain the selected medical images, not all of the plurality of medical images, thus reducing transmission time and storage requirements.

Optionally, the medical processing system is arranged for performing the follow-up examination of the patient, using the baseline images.

Optionally, the medical processing system is arranged for planning a follow-up scan of the follow-up examination, using the baseline images.

It will be appreciated by those skilled in the art that two or more of the above-mentioned embodiments, implementations, and/or aspects of the invention may be combined in any way deemed useful.

Modifications and variations of the workstation, imaging apparatus, method, and/or computer program product, which correspond to the described modifications and variations of the medical selection system and/or medical processing system can be carried out by a person skilled in the art on the basis of the present description. Moreover, modifications and variations of the medical processing system which correspond to the described modifications and variations of the medical selection system can be carried out by a person skilled in the art on the basis of the present description, and vice versa.

A person skilled in the art will appreciate that the method may be applied to multi-dimensional image data, e.g. to two-dimensional (2-D), three-dimensional (3-D) or four-dimensional (4-D) images. A dimension of the multi-dimensional image data may relate to time. For example, a three-dimensional image may comprise a time domain series of two-dimensional images. The image may be a medical image, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings, FIG. 1 shows a system comprising a medical selection system and medical processing system according to the present invention, and an image archiving system;

FIG. 2 shows a method according to the present invention; and

FIG. 3 shows a computer program product according to the present invention.

DETAILED DESCRIPTION OF EMBODIMENTS

FIG. 1 shows a communication network 010 comprising a medical selection system 100. The medical selection system 100 comprises a user input 110 for enabling a user to establish a selection of one or more medical images amongst a plurality of medical images. For that purpose, the user input 110 is shown to receive user input data 112 from a user by means of the user operating one or more user input devices, such as a keyboard 114, mouse 116, or touch-sensitive surface (not shown in FIG. 1). The medical selection system 100 further comprises a processor 120 for generating selection data 132 being indicative of said selection, and an output 130 for providing the selection data 132 to a medical processing system 150 for enabling the medical processing system 150 to select, based on the selection data 132, the one or more medical images amongst the plurality of medical images.

FIG. 1 further shows the communication network 010 comprising a medical processing system 150. The medical processing system 150 comprises an input 160 for obtaining the selection data 132 from the medical selection system 100. For that purpose, the output 130 of the medical selection system 100 is shown to be connected to the input 160 of the medical processing system 150. The medical processing system 150 further comprises a processor 170 for selecting the one or more medical images, based on the selection data 132 that is received from the medical selection system 100.

The operation of the medical selection system 100 and the medical processing system 150 may be explained as follows. The user input 110 of the medical selection system 100 enables a user to establish a selection of one or more medical images amongst a plurality of medical images 182. The user establishes the selection in order to select baseline images for use in a follow-up examination of the patient, which is prepared and/or performed on the medical processing system 150. Hence, the one or more medical images constitute a baseline selected by the user for use in said follow-up examination.

The user may establish the selection by, e.g., operating the mouse 116 in order to click on one or more of a plurality of thumbnails being shown on a display (not shown in FIG. 1). For that purpose, the medical selection system 100 may be connected to the display and may be arranged for displaying a graphical user interface on the display. The plurality of thumbnails may represent the plurality of medical images. By clicking on one or more of said thumbnails, the user may indicate his or her selection to the medical selection system 100. It is noted that various other ways of establishing the selection may be advantageously used. For example, the user may be shown additional information next to thumbnails, e.g., image metadata of each image such as an acquisition date, a file name, a patient name, etc. Also, the user possibly may not be provided with the plurality of medical images, or thumbnails thereof, at all, but rather may establish the selection merely from said image metadata or other information provided to the user on the display.

In this respect, it is noted that the medical selection system 100 may, but also may not, comprise the plurality of medical images. Instead of comprising the plurality of medical images, the medical selection system 100 may rather comprise thumbnails thereof, or other information. A reason for that may be that the plurality of medical images may constitute a large amount of data which otherwise may need to transmitted to, or obtained by, the medical selection system 100. In contrast, thumbnails may constitute a smaller amount of data, which may be easier or faster to transmit to the medical selection system 100.

The processor 120 of the medical selection system 100 then generates selection data 132 for enabling the selection of the user to be transmitted to the medical processing system 150. For that purpose, the selection data 132 is indicative of said selection.

For example, the selection data may comprise a series of identifiers that allow the one or more medical images to be identified, and subsequently selected, amongst the plurality of medical images, such as a DICOM Unique Identifier (UID), a patient name, a study identifier, a series number, an intended use, etc. The DICOM Unique Identifier may be a so-termed Study Instance UID, Series Instance UID, Image Instance UID, or other information which allows for the identification of the selection data based on the DICOM Information Model, i.e., as may be used by the so-termed Query Service Classes and Retrieve Service Classes. For example, when the selection data 132 identifies a specific study, the one or more medical images may be identified by, e.g., determining from the image metadata of the plurality of medical images whether an image is associated with said study. Moreover, when the selection data identifies an intended use, the one or more medical images may be identified by, e.g., determining from the image metadata of the plurality of medical images whether an image is associated with said intended use.

Alternatively, or additionally, the intended use may allow the medical processing system 150 to associate the selection data 132 with a particular one of multiple pluralities of medical images. Hence, the intended use may be included in the selection data 132 to serve as selection metadata which enables the medical processing system 150 to associate the selection data 132 with a particular plurality of medical images. In general, the selection metadata may be based on image metadata of the plurality of medical images. The metadata may be indicative of contents of the plurality of medical images, such as which patient is shown, at which date said images were acquired, the imaging modality used for acquiring said images, etc. The processor 120 may be arranged for generating the selection metadata by including at least a part of the image metadata 142. Therefore, at least a part of the selection metadata may be identical with a corresponding part of the image metadata of the plurality of medical images. This may allow the medical processing system 150 to associate the selection data with the particular plurality of images by determining a presence or lack of correspondences between selection metadata and image metadata.

FIG. 1 shows the medical selection system 100 obtaining the image metadata 142 from an image archiving system 180. The image archiving system 180 may, in addition to the image metadata 142, also comprise the plurality of medical images 182, and provide said plurality of medical images 182 to the medical processing system 150.

After having generated the selection data 132, the output 130 of the medical selection system 100 then provides the selection data to the medical processing system 150. The medical selection system 100 may provide the selection data 132 to the medical processing system 150 via a communications network. In order to provide compatibility of the selection data 132 with existing medical systems, such as an existing medical processing system 150, the processor 120 of the medical selection system 100 may be arranged for generating the selection data 132 in a format that is compatible with a pre-existing image communication standard. In particular, the processor 120 of the medical selection system 100 may be arranged for generating the selection data 132 in the DICOM format. This allows, if the communication network 010 is a DICOM network, the selection data 132 to be transmitted via the DICOM network. In this case, the medical selection system 100 and the medical processing system 150 may each be a DICOM application entity in the DICOM network 010, with the output 130 of the medical selection system 100 and the input 160 of the medical processing system 150 each constituting a DICOM network interface.

It is noted that processor 120 of the medical selection system 100 may be arranged for encoding the selection data 132 in an instance of a DICOM Service-Object Pair (SOP) Class. For example, the processor 120 may encode the selection data 132 in an Information Object of said DICOM Service-Object Pair Class. The DICOM Service-Object Pair Class may be a custom class, e.g., specifically arranged for encoding the selection data 132. The selection data 132 may be encoded in the Information Object by filling in attributes of the Information Object. Additionally, the DICOM Service-Object Pair Class may encode the selection metadata, in that specific attributes of the DICOM Service-Object Pair Class comprise information on, e.g., the study, series, or image. As a result, the DICOM Service-Object Pair Class may be easily paired with the plurality of medical images.

After transmission of the selection data 132, the medical processing system 150 receives the selection data via its input 160. Hence, the medical processing system 150 receives data being indicative of the selection of the one or more medical images amongst the plurality of medical images, as selected by the user using the medical selection system 100. The processor 170 of the medical processing system 150 may then associate the selection data 132 with the plurality of medical images, based on selection metadata included in the selection data. For example, the processor 170 may compare the selection metadata with image metadata of a particular plurality of medical images to determine whether the selection data 132 was generated for the particular plurality of medical images.

Having associated the selection data 132 with the particular plurality of medical images, the processor 170 of the medical processing system 150 may then select the one or more medical images amongst the plurality of medical images, based on the selection data. Based on the selection, the medical processing system 150 may then perform the follow-up examination of the patient, using the selected medical images as baseline images. Performing the follow-up examination may comprise performing a follow-up scan. In this case, the baseline images may be used for planning the follow-up scan, e.g., for ensuring that the follow-up images have a similar geometry as the baseline images to enable a visual comparison between both sets of medical images. Alternatively or additionally to using the baseline images in the planning of a follow-up scan, the baseline images may be used in the evaluation part of the follow-up examination, e.g., by simultaneously displaying the baseline images and the follow-up images for enabling a clinician to determine a change in the state of the patient. Alternatively, or additionally, said change may be determined automatically, e.g., using an image analysis technique.

The medical processing system 150 may comprise the plurality of medical images 182. For example, the medical processing system 150 may comprise a local data storage which, in turn, comprises the plurality of medical images 182. The plurality of medical images 182 may be originally stored in an image archiving system 180. The medical processing system 150 may be arranged for obtaining the plurality of medical images 182 from the image archiving system 180. Said obtaining is shown in FIG. 1, where the image archiving system 180 is shown to be connected to the input 160 of the medical processing system 150 in order to provide the plurality of medical images 182. Said obtaining may occur before the follow-up examination is planned, e.g., using a so-termed pre-fetching mechanism in which the plurality of medical images 180 is obtained, i.e., fetched, from the image archiving system 180 well before, or just before, said plurality of medical images 180 is to be used by the medical processing system 100. Alternatively, the input 160 of the medical processing system 150 may be arranged for obtaining specifically the one or more medical images from the image archiving system 180, based on the selection data 132. Hence, the medical processing system may not obtain all of the plurality of medical images 182, but instead specifically those selected by the user of the medical selection system 100. It is noted that the image archiving system 180 may be a DICOM database such as a PACS.

It is specifically noted that the present invention applies to selecting one baseline image as well as obtaining one follow-up image as well as comparing a single baseline image with a single follow-up image. Thus, it is not necessary to obtain multiple baseline images or multiple follow-up images, nor is it necessary to compare said multiple images.

The operation of the medical selection system 100 and the medical processing system 150 may be further explained within the context of automated planning of follow-up MR or CT scans, using baseline images. It is noted, however, that this is not a limitation, i.e., the present invention may be advantageously applied to any use of any suitable type of baseline images in a follow-up examination of a patient.

In the aforementioned context, a typical workflow may comprise selecting baseline images of the scheduled patient so as to plan a geometry of the follow-up scan that reproduces as closely as possible the geometry of the baseline images. The follow-up scan planning typically involves the technician performing multiple tasks before the actual scan takes place. For example, the available DICOM data may have to be queried and retrieved from one or more DICOM databases, while an exam card detailing how the follow-up scan should be performed may have to be selected in accordance with the scheduled procedure. Finally, one or more specific baseline images may need to be identified so that the acquisition of one or more follow-up images with, e.g., a similar geometry, may be planned.

The above workflow may be improved by means of a DICOM pre-fetch mechanism, which transfers a plurality of medical images to the medical processing system before the start of the follow-up examination. However, the above workflow typically involves the operator selecting the baseline scan manually after the plurality of medical images are transferred, e.g., at the console of the medical processing system. In case the operator is a technician, the technician may perform said selection based on the input from a clinician such as a radiologist. The selection of a correct baseline image is a non-trivial task, in particular if multiple images of the same patient are present on the medical processing system. This may cause time delays and errors. A selection of a wrong baseline image may lead to a decreased diagnostic value of the follow-up scan, unnecessary re-scans or a wrong diagnosis.

The present invention enables a specific DICOM series to be selected on the medical selection system for establishing a baseline scan for a scheduled procedure. The selection, encoded in the selection data, may then be used within scan planning software on the medical processing system to automatically select the correct DICOM series. The information about the correct baseline scan might be obtained by a medical expert. To this end, the medical expert may select the DICOM series in a PACS-like interface as provided by the medical selection system. The PACS-like interface may be provided by a RIS or another application running on the medical selection system The selection data may comprise information about the selected and transferred DICOM series, such as a unique series identifier, intended usage, or further parameters required by the planning software. Said information may be stored as a DICOM object, i.e., the selection data may constitute a DICOM object, which is then sent separately to the medical processing system, i.e., independently of the plurality of medical images. On the medical processing system, said information may be made available as a part of a DICOM modality worklist, or by means of a dedicated application running on the medical processing system that directly uses the DICOM object in the follow-up scan planning. In case the medical processing system is a RIS, said information may be made available to a further medical processing system such as a scanner, i.e., the DICOM modality worklist may be queried by accessing the RIS from a console of the scanner.

At this point in time, the selected DICOM series may be already available on the medical processing system due to the use of the earlier mentioned pre-fetch mechanism. Alternatively, the selected DICOM series itself could be transferred at this point, i.e., after receiving the selection data from the medical selection system.

A usage scenario of the above workflow may be the following. A hospital may comprise a RIS, a PACS, and a MR scanner, with the PACS being an embodiment of the image archiving system and the MR scanner being an embodiment of the medical processing system. The PACS may be equipped with the earlier mentioned pre-fetch mechanism.

In this usage scenario, a receptionist may enter information about the patients scheduled for the next day into the RIS. During the night, the pre-fetch mechanism of the PACS may transfer all previously acquired medical images of the scheduled patients to the MR scanner. Possibly, depending on rules used by the pre-fetch mechanism to select the DICOM data that is to be transferred, more medical images than required may be sent to the console of the MR scanner, as, in general, it is preferable to send more medical images than actually needed rather than missing a required medical image at the start of the follow-up examination. It is noted that the transfer time of the medical images is not crucial as the pre-fetching is generally performed a few hours before the follow-up examination starts.

In the morning, a radiologist and a technician may discuss the scheduled procedures. In case a follow-up scan is scheduled, the radiologist may check the PACS to determine which medical images were transferred to the MR scanner, and may, using a medical selection system, select a series of medical images. Information about the selected series of medical images may then be encoded into a dedicated DICOM object and sent to the MR scanner. When the technician subsequently starts the follow-up scan planning process on the MR scanner, the correct baseline scan is selected automatically.

It is noted that, in general, the medical selection system according to the present invention may additionally offer functionality of a RIS, PACS, DICOM pre-fetch system, and/or CDS system. As such, the medical selection system may effectively constitute said RIS, PACS, DICOM pre-fetch system and/or CDS system. The medical selection system may be an existing RIS, PACS, DICOM pre-fetch system and/or CDS system which has been modified in accordance with the present invention. The modification may comprise an additional software module or a software upgrade. Moreover, it is noted that the medical selection system may constitute a client-server system, comprising a client providing a display and user input means to the user, and a server arranged to send display data to the client and receive the user's input from the client. The server may constitute a client-server-based RIS, PACS, DICOM pre-fetch system and/or CDS system.

FIG. 2 shows a method 200 of generating selection data, comprising, in a first step titled "ENABLING USER TO ESTABLISH SELECTION", enabling 210 a user to establish a selection of one or more medical images amongst a plurality of medical images for establishing the one or more medical images as baseline images for use in a follow-up examination of a patient. The method 200 further comprises, in a second step titled "GENERATING SELECTION DATA", generating 220 selection data being indicative of said selection. The method 200 further comprises, in a third step titled "INCLUDING SELECTION METADATA", including 230 selection metadata in the selection data for enabling associating the selection data with the plurality of medical images. The method 200 further comprises, in a fourth step titled "PROVIDING THE SELECTION DATA TO MEDICAL PROCESSING SYSTEM", providing 240 the selection data to a medical processing system for enabling the medical processing system to select, based on the selection data, the one or more medical images amongst the plurality of medical images for use as baseline images in a follow-up examination of the patient.

The method 200 may correspond to an operation of the medical selection system 100, and is discussed in reference to said operation of the medical selection system 100. It is noted, however, that the method 200 may also be performed in separation of said medical selection system 100, e.g., using a different system or apparatus.

FIG. 3 shows a computer program product 260 comprising instructions for causing a processor system to perform the method according to the present invention. The computer program product 260 may be comprised on a computer readable medium 250, for example in the form of a series of machine readable physical marks and/or as a series of elements having different electrical, e.g., magnetic, or optical properties or values.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A medical selection system for generating selection data, the medical selection system comprising:
    a user input for enabling a user to establish a selection of one or more medical images amongst a plurality of medical images comprised in an image archiving system separate from the medical selection system for establishing the one or more medical images as baseline images for use in a follow-up examination of a patient;

a processor for (i) generating selection data being indicative of said selection, and (ii) including selection metadata in the selection data for enabling associating the selection data with the plurality of medical images; and an output for transmitting the selection data to a medical processing system separate from the medical selection system, the medical processing system being arranged for performing the follow-up examination of the patient for enabling the medical processing system to obtain, based on the selection data, the one or more medical images from the image archiving system for use as the baseline images in the performing of the follow-up examination of the patient.

2. The medical selection system according to claim 1, wherein the processor is arranged for generating the selection data having a format compatible with a pre-existing image communication standard.

3. The medical selection system according to claim 2, wherein the pre-existing image communication standard is DICOM.

4. The medical selection system according to claim 3, wherein the processor is arranged for encoding the selection data in an instance of a DICOM Service-Object Pair Class.

5. The medical selection system according to claim 4, wherein the processor is arranged for encoding the selection data in an Information Object of said DICOM Service-Object Pair Class.

6. The medical selection system according to claim 3, wherein the medical selection system forms a DICOM application entity in a DICOM network comprising the medical processing system, and output is a DICOM network interface of the DICOM application entity.

7. The medical selection system according to claim 1, further comprising an input for obtaining image metadata of the plurality of medical images, the image metadata being indicative of contents of the plurality of medical images, wherein the processor is arranged for generating the selection metadata, based on the image metadata.

8. The medical selection system according to claim 7, wherein the processor is arranged for generating the selection metadata by including at least a part of the image metadata.

9. The medical selection system according to claim 1, wherein the selection data comprises one of: a DICOM Unique Identifier (UID), a patient name, a study identifier, a series number, an intended use.

10. A workstation or imaging apparatus comprising the medical selection system according to claim 1.

11. A medical processing system for performing a follow-up examination of a patient, the medical processing system comprising:

a DICOM network interface for receiving selection data via a DICOM network from a medical selection system that is separate from the medical processing system, the selection data being indicative of a selection by a user of one or more medical images amongst a plurality of medical images stored in an image archiving system that is separate from the medical processing system;

a processor for (i) associating the selection data with the plurality of medical images, based on selection metadata included in the selection data, and (ii) obtaining said one or more medical images from the image archiving system, based on the selection data; and an X-ray Imaging, Computed Tomography (CT), Magnetic Resonance Imaging (MRI), Ultrasound (US), Positron Emission Tomography (PET), Single Photon Emission Computed Tomography (SPECT), or Nuclear Medicine (NM) medical imaging modality configured to perform a follow-up imaging examination using said one or more medical images obtained from the image archiving system as baseline images.

12. A communication network comprising:

an image archiving system comprising a plurality of medical images;

the medical processing system according to claim 11 for performing a follow-up examination of a patient; and a medical selection system for providing selection data to the medical processing system for enabling the medical processing system to obtain, based on the selection data, one or more medical images from the image archiving system for use as the baseline images in the performing of the follow-up examination of the patient.

13. A workstation or imaging apparatus comprising the medical processing system according to claim 11.

14. A communication network comprising:

an image archiving system comprising a plurality of medical images;

a medical processing system for performing a follow-up examination of a patient; and a medical selection system according to claim 11 for providing selection data to the medical processing system for enabling the medical processing system to obtain, based on the selection data, one or more medical images from the image archiving system for use as the baseline images in the performing of the follow-up examination of the patient.

15. A method of generating selection data, comprising:

with a user input device of a medical selection system, enabling a user to establish a selection of one or more medical images amongst a plurality of medical images comprised in an image archiving system separate from the medical selection system for establishing the one or more medical images as baseline images for use in a follow-up examination of a patient;

with at least one processor of the medical selection system, generating selection data being indicative of said selection;

with the at least one processor of the medical selection system, including selection metadata in the selection data for enabling associating the selection data with the plurality of medical images; and with an output device of the medical selection system, providing the selection data to a medical processing system separate from the medical selection system for enabling the medical processing system to obtain, based on the selection data, the one or more medical images from the image archiving system for use as baseline images in a follow-up examination of the patient.

16. A non-transitory computer readable medium comprising instructions for causing the at least one processor to perform the method according to claim 15.

17. The method according to claim 15, further including:

with an input, obtaining image metadata of the plurality of medical images, the image metadata being indicative of contents of the plurality of medical images, wherein the processor is arranged for generating the selection metadata, based on the image metadata.

18. A communication network comprising:

an image archiving system comprising a plurality of medical images;

a medical processing system separate from the image archiving system and configured to generate selection data, the medical selection system including:

a user input configured to enable a user to establish a selection of one or more medical images amongst a plurality of medical images comprised in the image archiving system for establishing the one or more medical images as baseline images for use in a follow-up examination of a patient; and at least one processor programmed to: (i) generate selection data being indicative of said selection, and (ii) include selection metadata in the selection data for enabling associating the selection data with the plurality of medical images; and a transmitter configured to transmit the selection data;

a medical selection system separate from the image archiving system and separate from the medical processing system and configured to provide selection data to the medical processing system, the medical selection system including:

a receiver configured to receive the selection data from the transmitter of the medical selection system, the selection data being indicative of a selection by a user of one or more medical images amongst a plurality of medical images comprised in an image archiving system; and at least one processor programmed to (i) associate the selection data with the plurality of medical images, based on selection metadata included in the selection data, and (ii) obtain said one or more medical images from the image archiving system, based on the selection data, for use as a baseline images in the performing of the follow-up examination.

19. The communication network according to claim 18, wherein the medical processing system further includes a receiver configured to receive image metadata of the plurality of medical images, the image metadata being indicative of contents of the plurality of medical images, and wherein the at least one processor of the medical processing system is further programmed to generate the selection metadata, based on the image metadata.

20. The communication network according to claim 19, wherein the at least one processor of the medical processing system is programmed to generate the selection metadata by including at least a part of the image metadata.

* * * * *